United States Patent [19]

Diehl et al.

[11] Patent Number: 4,476,320

[45] Date of Patent: Oct. 9, 1984

[54] PROCESS FOR THE PREPARATION OF FLUOROAROMATIC COMPOUNDS SUBSTITUTED IN THE O-POSITION

[75] Inventors: Herbert Diehl, Leverkusen; Heinrich Pelster, Odenthal; Hubert Habetz, Leverkusen, all of Fed. Rep. of Germany

[73] Assignee: Bayer Aktiengesellschaft, Leverkusen, Fed. Rep. of Germany

[21] Appl. No.: 431,856

[22] Filed: Sep. 29, 1982

[30] Foreign Application Priority Data

Oct. 21, 1981 [DE] Fed. Rep. of Germany ....... 3141659

[51] Int. Cl.$^3$ .............................................. C07C 69/76
[52] U.S. Cl. ...................................... 560/103; 560/65; 562/474; 562/493; 568/655; 570/127
[58] Field of Search ................. 560/103, 65; 562/474, 562/493; 568/655; 570/127

[56] References Cited

FOREIGN PATENT DOCUMENTS 22959 1/1981 European Pat. Off. .

OTHER PUBLICATIONS

Journal of Organic Chemistry, vol. 44, No. 9, 1979, pp. 1572–1574.

*Primary Examiner*—Paul J. Killos
*Attorney, Agent, or Firm*—Spring, Horn, Kramer & Woods

[57] ABSTRACT

Ortho-substituted fluoroaromatic compounds are prepared by reaction of corresponding anilines, which are substituted in the o-position, with alkyl nitrites in the presence of alcohols and/or ethers and in the presence of boron trifluoride or boric acid esters and hydrogen fluoride, and by isolation and decomposition of the diazonium tetrafluoborate produced.

16 Claims, No Drawings

PROCESS FOR THE PREPARATION OF FLUOROAROMATIC COMPOUNDS SUBSTITUTED IN THE O-POSITION

The invention relates to a process for the preparation of fluoroaromatic compounds substituted in the o-position from the corresponding aromatic amines.

The preparation of aromatic fluorine compounds, having fluorine bonded to the nucleus, from the corresponding amines either by diazotization in anhydrous hydrofluoric acid and subsequent heating of the diazonium fluoride solution or by precipitation of the sparingly soluble diazonium tetrafluoborates and their thermal decomposition, is known (compare Houben-Weyl, Methoden der organischen Chemie (Methods of Organic Chemistry), volume V/3, page 213 et seq. (1962)).

Whilst diazotization in anhydrous hydrofluoric acid in fact gives good results with simple aromatic amines, only moderate yields are obtained with amines which have a substituent in the o-position to the amino group, which contains halogen or oxygen. Thus, for example, according to U.S. Pat. No. 3,950,444, 2-bromofluorobenzene is obtained in only a maximum 66% yield and 2-chlorofluorobenzene is obtained in only 28% yield when 2-bromoaniline or 2-chloroaniline respectively is diazotized in anhydrous hydrofluoric acid and subsequently the diazonium fluoride is thermally decomposed.

In contrast, the preparation of aromatic fluorine compounds via the diazonium tetrafluoborates has substantially wider application. However, it is disadvantageous that the decomposition reaction of many diazonium tetrafluoborates can only be carried out on a relatively small scale. For this reason, the process has not yet found industrial application in contrast to diazotization in anhydrous hydrofluoric acid (compare Houben-Weyl, Methoden der organischen Chemie (Methods of Organic Chemistry), volume V/3, page 216 (1962)). In addition, this mode of preparation, in which the diazonium tetrafluoborates are prepared predominantly in an aqueous system with an alkali metal nitrite, alkyl nitrite or nitrosyl chloride as the diazotizing agent and tetrafluoboric acid or alkali metal tetrafluoborate as the source of the tetrafluoborate ions has the additional disadvantage that, due to the corrosive nature of the reaction medium (aqueous tetrafluoboric acid), only special and costly apparatus materials can be used.

The preparation of aromatic diazonium tetrafluoborates in non-aqueous systems by reaction of the corresponding amines with tert.-butyl nitrite and BF$_3$-etherate gives, according to J. Org. Chem. 44, (9), 1572 (1979) generally good yields, if the reaction is carried out in anhydrous organic solvents, such as tetrahydrofuran, dimethoxyethane and diethyl ether, preferably dichloromethane.

Since, in this method, a large excess of BF$_3$-etherate is used, this method is not suitable for the preparation of aromatic diazonium tetrafluoborates on an industrial scale for economic reasons. In addition, by this method, only unsatisfactory yields of, for example, 3-bromo-4-fluorotoluene are obtained, since the corresponding diazonium tetrafluoborate is contaminated with the starting material 2-bromo-4-methylanilinium tetrafluoborate (compare Example 1a)/comparison example).

A process has now been found for the preparation of fluoroaromatic compounds substituted in the o-position of the formula

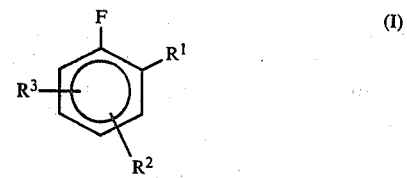

in which
R$^1$ represents halogen, or represents a trihalogenomethyl, alkoxy, trifluoromethoxy, carboxyl or an alkoxycarbonyl group and R$^2$ and R$^3$ are identical or different and represent hydrogen, halogen, an alkyl, trihalogenomethyl, alkoxy, trifluoromethoxy, carboxyl or an alkoxycarbonyl group,
which is characterized in that an aniline substituted in o-position of the formula

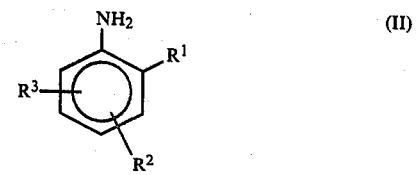

in which
R$^1$, R$^2$ and R$^3$ have the abovementioned meaning, is reacted with an alkyl nitrite in the presence of an alcohol and/or ether, optionally with the addition of an inert organic diluent, and in the presence of boron trifluoride and hydrogen fluoride at temperatures from $-20°$ to $+10°$ C., the diazonium tetrafluoborate produced is isolated and the latter, optionally after drying, is decomposed in the presence of an inert heat-transfer medium at an elevated temperature.

The halogens which may be mentioned are: fluorine, chlorine, bromine and iodine, preferably fluorine, chlorine and bromine, particularly preferably bromine; the alkyl radicals are those having 1 to 10, preferably 1 to 4, carbon atoms, such as the methyl, ethyl, n-propyl, iso-propyl, n-butyl, iso-butyl, tert.-butyl, n-pentyl, iso-pentyl, hexyl, heptyl, octyl, nonyl and the decyl radical, preferably the methyl, ethyl, n-propyl and the n-butyl radical; the trihalogenomethyl radicals are the trifluoromethyl and the trichloromethyl radical, preferably the trifluoromethyl radical; the alkoxy radicals are those having 1 to 10, preferably 1 to 3, carbon atoms, such as the methoxy, ethoxy, propoxy, butoxy and the pentoxy radical preferably the methoxy, ethoxy and the propoxy radical, and the alkoxycarbonyl radicals are those having 1 to 10, preferably 1 to 5, carbon atoms, such as the methoxycarbonyl, ethoxycarbonyl, carboxycarbonyl, butoxycarbonyl, pentoxycarbonyl and the hexoxycarbonyl radical, preferably the methoxycarbonyl, ethoxycarbonyl and the propoxycarbonyl radical.

In the process according to the invention, the following can be used as o-substituted anilines of the formula (II): 2-bromoaniline, 2-methoxyaniline, 2-ethoxycarbonylaniline, 2-trifluoromethyl-4-bromoaniline, 2-chloroaniline, 2-bromo-4-methylaniline, 2,4-dichloro-5-aminotoluene and 2-bromo-4,6-dimethylaniline.

The following are preferably used: 2-bromo-4-methylaniline, 2-bromo-4,6-dimethylaniline and 2-chloroaniline.

The alkyl nitrites which can be used in the process according to the invention are those having 1 to 10, preferably 1 to 5, carbon atoms, such as methyl nitrite, ethyl nitrite, isopropyl nitrite, isobutyl nitrite, isoamyl nitrite, isohexyl nitrite and isoheptyl nitrite, preferably methyl nitrite, isopropyl nitrite and isobutyl nitrite.

The amount of alkyl nitrites to be used is not critical. In general, about 1.0 to 2.0 mols, preferably 1.05 to 1.15 mols of alkyl nitrite are used per mol of aromatic amino compound.

The alcohols which can be used in the process according to the invention are those having 1 to 10, preferably 1 to 5, carbon atoms. Alkanols can be used such as methanol, ethanol, n-propanol, iso-propanol, n-butanol, iso-butanol, tert.-butanol, n-pentanol, iso-pentanol, n-hexanol and n-heptanol, preferably methanol, ethanol, isopropanol and iso-butanol.

The ethers which can be used in the process according to the invention are those having 4 to 10, preferably 4 to 8, carbon atoms, such as tetrahydrofuran, dimethoxyethane and diethoxyethane, preferably tetrahydrofuran and dimethoxyethane.

The alcohols and the ethers can be used either alone or as a mixture one with another in the process according to the invention, it being possible for the alcohols and the ethers to be mixed together in any desired ratio.

The amount of the alcohols and/or ethers to be used can vary within wide ranges. Customarily, 200 g to 1,000 g, preferably 250 to 500 g, relative to 100 g of aniline derivative, are used.

The process according to the invention can, if appropriate, be carried out with the addition of an inert organic diluent, such as dichloromethane, chlorobenzene and/or toluene, preferably dichloromethane. In this context, in general, 100 to 1,000 g, relative to 100 g of aniline derivate, of inert organic diluent are added to the alcohol and/or ether used.

The amount of boron trifluoride and hydrogen fluoride which is used in the process according to the invention can vary within wide limits. Customarily, 1.0 to 2.0, preferably 1.05 to 1.50 mols, of each of boron trifluoride and hydrogen fluoride are used per mol of aromatic amine. Advantageously, the reaction is carried out with a molar excess of boron trifluoride and hydrogen fluoride relative to the aromatic amine used.

The molar ratio of boron trifluoride to hydrogen fluoride can also vary within wide ranges. However, it is advantageous to use the boron trifluoride in a slight excess compared to hydrogen fluoride. Thus, in general, 1.01 to 1.50 mols, preferably 1.05 to 1.20 mols, of boron trifluoride is employed per mol of hydrogen fluoride.

In another variant of the process according to the invention, instead of with boron trifluoride and hydrogen fluoride, the reaction can also be carried out with boric acid esters, such as trimethyl, triethyl, triisopropyl and/or tributyl borate, preferably triisopropyl borate and/or triisobutyl borate, and hydrogen fluoride. In this variant, the boric acid esters and the hydrogen fluoride are used in the appropriate molar ratio to one another and in an amount corresponding to the boron trifluoride and hydrogen fluoride in the process according to the invention.

The diazotization according to the invention is customarily carried out at temperatures from about $-20°$ to $+20°$ C., preferably up to $+5°$ C.

The diazonium tetrafluoborate formed in the reaction according to the invention is isolated in a customary manner, for example, by filtration or centrifugation, and, optionally after drying, is thermally decomposed in the presence of a heat-transfer medium.

Examples of heat-transfer media are halogenated aromatic compounds, such as chlorobenzene, dichlorobenzenes and/or 1-chloronaphthalene and also paraffin oil and/or alkylated aromatic compounds, such as xylene and triisopropylbenzene.

Paraffin oil and triisopropylbenzene are preferably employed as the heat-transfer medium.

The thermal decomposition of the diazonium tetrafluoborates is advantageously carried out at a temperature which is up to about 50° C. above the decomposition temperature of the particular diazonium tetrafluoborate. In general, the decomposition is carried out at about 100° to 200° C., preferably 100° to 150° C.

The boron trifluoride liberated during the decomposition can, according to a preferred procedure, be absorbed in one or more of the previously mentioned alcohols and/or ethers, and, in this manner, be returned to the reaction.

The process according to the invention can be carried out in such a manner that initially the aromatic amine and then the alkyl nitrite, or vice versa, first the alkyl nitrite and subsequently the aromatic amine, is added to the initially introduced alcohol and/or ether containing boron trifluoride or boric acid ester and hydrogen fluoride. Furthermore, it is possible to introduce the alcohol and/or ether together with boron trifluoride or boric acid ester and the aromatic amine initially and finally to meter in the hydrogen fluoride and alkyl nitrite. However, it has been found to be particularly advantageous to meter synchronously the aromatic amine and the alkyl nitrite into the initially introduced alcohol and/or ether containing boron trifluoride and hydrogen fluoride or boric acid ester and hydrogen fluoride.

The reaction mixture is cooled down to about $-10°$ to $0°$ C., and, after completion of the reaction, the diazonium tetrafluoborate which precipitates from the solvent is filtered off. After washing the diazonium tetrafluoborate with, for example, a mixture of iso-butanol and methanol or with an inert solvent, the diazonium tetrafluoborate is optionally dried in vacuo and subsequently decomposed by introduction into, for example, initially introduced paraffin oil which is heated up to about 50° C. above the decomposition temperature of the particular diazonium tetrafluoborate. After decomposition of the diazonium tetrafluoborate, the aromatic fluorine compound is distilled off in vacuo, the distillate is treated with a compound having a basic reaction, for example, calcium oxide, the basic compound is filtered off and the aromatic fluorine compound is isolated by renewed distillation.

The boron trifluoride liberated in the decomposition of the diazonium tetrafluoborate is advantageously absorbed in the alcohol and/or ether used for the reaction and returned to the reaction.

By the process according to the invention, fluoroaromatic compounds substituted in the o-position are obtained in good yields (up to 90% of theory) and high purities ( 95%). This is particularly surprising, since it has hitherto only been possible to an unsatisfactory extent industrially to exchange the amino group by fluorine via a diazonium compound, when a substituent was present in the o-position to the amino group which contained halogen or oxygen (compare Houben-Weyl, Methoden der organischen Chemie (Methods of Organic Chemistry), volume V/3, page 214, 216 (1962)).

The o-substituted fluoroaromatic compounds prepared by the process according to the invention are valuable starting materials for the preparation of active substances.

Thus, 3-bromo-4-fluorotoluene serves as a precursor for the preparation of 4-fluoro-3-phenoxytoluene (German Offenlegungsschriften Nos. 2,837,525 and 2,932,093), which in turn is used as a parent substance for the preparation of insecticides (German Offenlegungsschriften Nos. 2,837,524 and 2,844,816; European Pat. No. 9,708).

The following examples are intended to illustrate the process according to the invention, but do not restrict it to these examples.

EXAMPLE 1

(comparison example carried out in accordance with J. Org. Chem. 44 (9), 1572 (1979))

(a) Dichloromethane

A solution of 92 g of 2-bromo-4-methylaniline in 500 ml of dichloromethane is added dropwise to 105.4 g of boron trifluoride etherate at $-15°$ C. The mixture is then stirred for 30 minutes at this temperature and is then allowed to rise to $+5°$ C.

A solution of 81 g of tert.-butyl nitrite in 250 ml of dichloromethane is now added dropwise at $+5°$ C., (within 1 hour). The mixture is then stirred for 15 minutes at $+5°$ C. and the precipitated salt is filtered off with suction. The solid material is washed with about 200 ml of dichloromethane and dried at room temperature in vacuo. 127 g of a crystalline solid material are obtained which contains 90 to 95% of 2-bromo-4-methylbenzenediazonium tetrafluoborate, 81 to 85% of theory (remainder: 2-bromo-4-methylanilinium tetrafluoborate).

Decomposition in accordance with Example 6 provides 53 g of 3-bromo-4-fluorotoluene in addition to large amounts of resinous by-products (yield: 56.6% of theory over the two stages).

(b) Tetrahydrofuran 93 g of 2-bromo-4-methylaniline are added dropwise to a solution of 51 g of boron trifluoride in 200 ml of tetrahydrofuran at $-15°$ C. The mixture is then stirred for 30 minutes and 62 g of tert.-butyl nitrite are then added dropwise at 0° to 5° C. The mixture is then stirred for 1 hour at 0° C. and the residue is filtered off.

The filter cake is washed with about 10 ml of cold tetrahydrofuran and then dried at room temperature in vacuo.

112 g of 2-bromo-4-methylbenzenediazonium tetrafluoborate (78.6% of theory) are obtained.

Decomposition in accordance with Example 6 provides 63 g of 3-bromo-4-fluorotoluene (85% of theory). The yield over the two stages is 66.8% of theory.

EXAMPLE 2

186 g of 2-bromo-4-methylaniline are added dropwise to a solution of 71 g of boron trifluoride and 20.4 g of hydrogen fluoride in 315 g of i-propanol at 0° to 5° C. and, at the same time, 67.0 g of methyl nitrite are passed in.

The mixture is then stirred for 1 hour at 0° C. and the precipitated diazonium salt is filtered off. The solid material is washed with a total of 120 g of i-propanol and then dried at room temperature in vacuo.

In this manner, 275 g (96.5% of theory) of 2-bromo-4-methylbenzenediazonium tetrafluoborate are obtained.

Decomposition in accordance with Example 6 provides 3-bromo-4-fluorotoluene in a yield of 92.4% of theory.

EXAMPLE 3

Initially 71 g of triisopropyl borate and subsequently 67.5 g of 2-bromo-4-methylaniline are added dropwise at 0° C. with cooling to a solution of 30 g of hydrogen fluoride in 150 g of i-propanol. The mixture is then stirred for 30 minutes at 0° C. and 36 g of i-propyl nitrite are then added dropwise at $-5°$ to 0° C. within 15 minutes. The mixture is stirred for a further 15 minutes, filtered off with suction and the residue is washed with a little cold i-propanol.

After drying in vacuo at room temperature, 98.5 g of 2-bromo-4-methylbenzenediazonium tetrafluoborate are obtained (96% of theory).

Decomposition in accordance with Example 6 provides 3-bromo-4-fluorotoluene in a yield of 92.4% of theory.

EXAMPLE 4

84 g of 2-bromo-4-methylaniline and 54.5 g of i-butyl nitrite are added dropwise simultaneously from 2 dropping funnels at $-5°$ to 0° C. to a solution of 37 g of boron trifluoride and 10.3 g of hydrogen fluoride in 160 g of dimethoxyethane (duration 1 hour). The mixture is then stirred for 15 minutes at 0° C. and filtered off with suction. The crystalline diazonium salt is washed with 50 ml of cold dimethoxyethane and then dried at room temperature in vacuo.

Yield: 122.5 g (86% of theory).

Decomposition in accordance with Example 6 provides 3-bromo-4-fluorotoluene in a yield of 92.4% of theory.

EXAMPLE 5

186 g of 2-bromo-4-methylaniline and 122 g of i-butyl nitrite (93.5% strength in i-butanol) are added dropwise simultaneously from two dropping funnels to a solution of 71 g of boron trifluoride and 20.4 g of hydrogen fluoride in 400 g of i-butanol at 0° to 5° C. (duration about 3 hours).

The mixture is then stirred for 1 hour at 0° C., filtered off and the solid material is washed with 150 g of iso-butanol.

After drying at room temperature in vacuo, 280 g of 2-bromo-4-methylbenzenediazonium tetrafluoborate are obtained (98.2% of theory).

Decomposition in accordance with Example 6 provides 3-bromo-4-fluorotoluene in a yield of 92.4% of theory.

EXAMPLE 6

143 g of 2-bromo-4-methylbenzenediazonium tetrafluoborate (prepared in accordance with Examples 2-5) are introduced into 80 g of paraffin oil at 120° to 125° C. in the course of 5 hours.

The gas evolved (boron trifluoride and nitrogen) is passed through a washer which contains 100.0 g of i-butanol at 0° C.

After completion of the introduction, the reaction mixture is then stirred for approximately a further 1 hour at 125° to 130° C.

Subsequently, volatile components are distilled off in vacuo.

The distillate is treated with 1 g of calcium oxide and filtered. In this manner, 88.2 g of 3-bromo-4-fluorotoluene of 99% purity are obtained (yield: 92.4% of theory).

The content of the washer for the evolved gas (25.2% $BF_3$ in iso-butanol, 130 g) can, after adjustment to the required concentration, be used for the preparation of 2-bromo-4-methylbenzenediazonium tetrafluoborate in accordance with Example 5.

The recycling rate has been found to be 96.5% of theory.

EXAMPLE 7

855 g of 2-bromo-4-methylbenzenediazonium tetrafluoborate are introduced in 85 g of 1,3,5-triisopropylbenzene at 125° to 130° C. in the course of 10 hours.

After completion of the introduction, the mixture is maintained at 125° to 130° C. for a further 1 hour (completion of evolution of gas). Subsequently, volatile components are distlled off in vacuo. The distillate is neutralized with calcium oxide and purified by rectification. 474.5 g of 3-bromo-4-fluorotoluene (98.8% pure) are obtained, that is to say 82.7% of theory.

The residue from distillation (1,3,5-triisopropylbenzene, 88.4 g) can be recycled.

The $BF_3$ produced in the decomposition is absorbed in alcohol and can thus be returned to the process as required (yield: >90% of theory).

EXAMPLE 8

145 g of 2-bromo-4-methylbenzenediazonium tetrafluoborate are introduced to 100 g of 1-chloronaphthalene at 125° to 130° C. in the course of 3 hours.

After completion of the introduction, the mixture is stirred for a further 1 hour at 125° to 130° C.

Subsequently, the 3-bromo-4-fluorotoluene produced is distilled off under reduced pressure. After neutralization with calcium oxide, 72.5 g of 3-bromo-4-fluorotoluene (76.4% of theory) are obtained.

The boron trifluoride produced is absorbed in i-propanol (>90% of theory), and can thus be used again for the preparation of the starting material (see Example 2).

The residue (1-chloronaphthalene and resinous by-products) can be recycled after neutralization with calcium oxide and distillation.

EXAMPLE 9

The following diazonium fluoborates have been prepared in accordance with Example 5:

| Benzenediazonium tetrafluoborate derivative | Yield (% of theory) |
| --- | --- |
| 2-Bromo | 97.4 |
| 2-Chloro | 96.7 |
| 2-Bromo-4,6-dimethyl | 99.0 |
| 2-Methoxy | 92.3 |
| 2-Ethoxycarbonyl | 97.7 |
| 2-Trifluoromethoxy | 97.1 |
| 2-Trifluoromethyl-4-bromo | 93.5 |

EXAMPLE 10

The following fluorobenzene derivatives have been prepared in accordance with Example 6:

| Fluorobenzene derivative | Yield (% of theory) |
| --- | --- |
| 2-Bromo | 84.1 |
| 2-Chloro | 81.2 |
| 2-Bromo-4,6-dimethyl | 80.5 |
| 2-Methoxy | 58.7 |
| 2-Ethoxycarbonyl | 65.7 |
| 2-Trifluoromethyl-4-bromo | 88.5 |

EXAMPLE 11

88 g of 2,4-dichloro-5-aminotoluene in 330 g of toluene are added dropwise to and 50 g of methyl nitrite are passed into a solution of 13 g of hydrogen fluoride and 44 g of boron trifluoride in 275 g of i-propanol at 0° C. to +5° C.

After completion of the introduction, the mixture is stirred for a further 30 minutes at 0° C.

The residue is then filtered off with suction, washed with cold i-propanol (100 g) and subsequently dried at room temperature in vacuo.

Yield: 128.5 g of 2,4-dichloro-5-methylbenzenediazonium tetrafluoborate (93.5% of theory).

EXAMPLE 12

50 g of 2,4-dichloro-5-methylbenzenediazonium tetrafluoborate are introduced in small portions to 20 g of 2,4-dichloro-5-fluorotoluene at 160°–165° C. in the course of about 3 hours. After completion of the evolution of gas, the residue is distilled under reduced pressure.

After neutralization with calcium oxide, 28.5 g of 2,4-dichloro-5-fluorotoluene (97% of theory) are obtained.

The boron trifluoride produced is absorbed in i-propanol (>90% of theory) and can be used again in this form for the preparation of the starting material (see Example 11).

What is claimed is:

1. A process for the preparation of a fluoroaromatic compound substituted in the ortho position of the formula

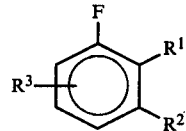

wherein
$R^1$ represents halogen, or represents a trihalogenomethyl, alkoxy, trifluoromethoxy, carboxyl or an alkoxycarbonyl group and
$R^2$ and $R^3$ are identical or different and independently represent hydrogen, halogen, alkyl, trihalogenomethyl, alkoxy, trifluoromethoxy, carboxyl or an alkoxycarbonyl group, which comprises contacting an aniline substituted in the ortho-position of the formula

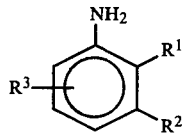

wherein

R¹, R² and R³ have the previously assigned significance, with an alkyl nitrite in the presence of an alcohol and/or ether, in the presence of hydrogen fluoride and in the presence of boron trifluoride or a boric acid ester, at a temperature from −20° to +10° C. whereby to form a diazonium tetrafluoborate, isolating said diazonium tetrafluoborate and thereafter decomposing said diazonium tetrafluoborate by contacting the same with an inert heat transfer medium at an elevated temperature.

2. A process according to claim 1, wherein the aniline substituted in the ortho-position is reacted with the alkyl nitrite in the presence of a boric acid ester and hydrogen chloride.

3. A process according to claim 1, wherein the aniline substituted in the ortho-position is reacted with the alkyl nitrite in the presence of boron trifluoride and hydrogen fluoride.

4. A process according to claim 1, wherein boron trifluoride liberated as a result of the decomposition of said diazonium tetrafluoborate is absorbed in an alcohol and/or ether and returned to the reaction.

5. A process according to claim 1, wherein said ortho-substituted aniline is selected from the group consisting of 2-bromoaniline, 2-methoxyaniline, 2-ethoxycarbonylaniline, 2-trifluoromethyl-4-bromoaniline, 2-chloroaniline, 2-bromo-4-methylaniline, 2,4-dichloro-5-aminotoluene and 2-bromo-4,6-dimethylaniline.

6. A process according to claim 1, wherein 1.0 to 2.0 mols of alkyl nitrite are employed per mol of ortho-substituted analine.

7. A process according to claim 1, wherein combined amounts of alcohol in ether is 200 to 1,000 g relative to 100 g of ortho-substituted aniline.

8. A process according to claim 1, wherein 1.0 to 2.0 mols of boron trifluoride or boric acid triester or mixture thereof and 1.0 to 2.0 mols of hydrogen fluoride are employed per mol of ortho-substituted aniline.

9. A process according to claim 1, wherein the process is carried out employing 1.01 to 1.5 mols of boron trifluoride or boric acid ester or mixture thereof per mol of hydrogen fluoride.

10. A process according to claim 1, wherein the heat transfer medium is a halogenated aromatic compound, paraffin oil, alkylated aromatic compound or mixture thereof.

11. A process according to claim 1, wherein said diazonium tetrafluoborate is thermally decomposed at a temperature of 100° to 200° C.

12. A process according to claim 1, wherein the process is carried out in the presence of an alcohol.

13. A process according to claim 12, wherein said alcohol is methanol, ethanol, n-propanol, iso-propanol, n-butanol, iso-butanol, tert.-butanol, n-pentanol, iso-pentanol, n-hexanol or n-heptanol or a mixture thereof.

14. A process according to claim 8, wherein the process is carried out in the presence of an alcohol and said alcohol is methanol, ethanol, n-propanol, iso-propanol, n-butanol, iso-butanol, tert.-butanol, n-pentanol, iso-pentanol, n-hexanol or n-heptanol or a mixture thereof.

15. A process according to claim 1, wherein the alcohol or ether is employed in an amount of 200 to 1000 g per 100 g of ortho-substituted aniline.

16. A process according to claim 14, wherein said alcohol is employed in an amount of 200 to 1000 g per 100 g of said ortho-substituted aniline.

* * * * *